United States Patent
Tian et al.

(10) Patent No.: US 9,168,516 B2
(45) Date of Patent: Oct. 27, 2015

(54) SOLVOTHERMAL SYNTHESIS PROCESS OF SAPO MOLECULAR SIEVES AND CATALYSTS PREPARED THEREBY

(75) Inventors: Peng Tian, Dalian (CN); Zhongmin Liu, Dalian (CN); Ying Zhang, Dalian (CN); Dong Fan, Dalian (CN); Xiong Su, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 306 days.

(21) Appl. No.: 13/976,458
(22) PCT Filed: Jun. 24, 2011
(86) PCT No.: PCT/CN2011/076332
§ 371 (c)(1), (2), (4) Date: Jun. 26, 2013
(87) PCT Pub. No.: WO2012/088854
PCT Pub. Date: Jul. 5, 2012

(65) Prior Publication Data
US 2013/0280161 A1   Oct. 24, 2013

(30) Foreign Application Priority Data
Dec. 29, 2010  (CN) .......................... 2010 1 0610515

(51) Int. Cl.
*C01B 39/54*  (2006.01)
*B01J 29/85*  (2006.01)
(Continued)

(52) U.S. Cl.
CPC ................ *B01J 29/85* (2013.01); *C01B 37/08* (2013.01); *C01B 39/54* (2013.01); *C07C 1/20* (2013.01); *C07C 2529/85* (2013.01)

(58) Field of Classification Search
CPC ............ B01J 29/85; C01B 39/54; C07C 1/02; C07C 2529/85
See application file for complete search history.

(56) References Cited

U.S. PATENT DOCUMENTS

| 4,310,440 A | 1/1982 | Wilson et al. |
| 5,208,005 A * | 5/1993 | Miller .......................... 423/702 |

(Continued)

FOREIGN PATENT DOCUMENTS

| CN | 1351960 A | 6/2002 |
| CN | 1488579 A | 4/2004 |

(Continued)

OTHER PUBLICATIONS

A. F. Ojo et al., Synthesis and Properties of SAPO-5 Molecular Sieves, J. Chem. Soc. Faraday Trans., 1992, 88, 105-112.
(Continued)

*Primary Examiner* — David M Brunsman
(74) *Attorney, Agent, or Firm* — Enshan Hong; VLP Law Group LLP

(57) ABSTRACT

A solvothermal synthesis process of the SAPO molecular sieves and catalysts prepared thereby are provided. The synthesis process comprises the following steps: a) an organic amine, an aluminum source, a phosphorus source, a silicon source, and water are mixed in a molar ratio of 6-30:1:0.5-5:0.01-1.0:0.1-15, to obtain an initial mixture for preparing the SAPO molecular sieves, wherein the molar ratio of water to the organic amine is less than 2.0; b) the initial mixture obtained in the step a) is maintained at 30-60° C. to and aged with stirring for not more than 24 hours, to obtain an initial gel; c) the initial gel obtain in the step b) is crystallized at 150-250° C. for 0.5-15 days. The SAPO molecular sieves prepared thereby are used, after being calcined at 400-700° C. in air, as catalysts for acid-catalyzed reactions or for conversion reactions of oxygen-containing compounds to olefins.

19 Claims, 1 Drawing Sheet

(51) Int. Cl.
  *C07C 1/20*    (2006.01)
  *C01B 37/08*   (2006.01)

(56) References Cited

U.S. PATENT DOCUMENTS

2003/0129128 A1* 7/2003 Strohmaier et al. .......... 423/716
2010/0317910 A1* 12/2010 Mies et al. .................... 585/739

FOREIGN PATENT DOCUMENTS

| | | |
|---|---|---|
| CN | 101121529 A | 2/2008 |
| CN | 101121530 A | 2/2008 |
| CN | 101503201 A | 8/2009 |
| CN | 101993093 A | 3/2011 |
| JP | 59-035018 A | 2/1984 |
| JP | 60-151212 A | 8/1985 |
| JP | 2007-269601 A | 10/2007 |
| JP | 2008-030966 A | 2/2008 |
| JP | 2009-538810 A | 11/2009 |
| JP | 2012-012288 A | 1/2012 |
| JP | 2012-529414 A | 11/2012 |
| KR | 10-2008-01142332 | 12/2008 |
| WO | 8909749 A1 | 10/1989 |

OTHER PUBLICATIONS

W. Zheming et al., A Highly Active Si-Enriched Pt-SAPO-11 Catalyst Synthesized by the Solvothermal Method for the n-Dodecane Hydroisomerization, Chinese Journal of Catalysis, 2005, 26, 268-270.
First Office Action issued by the Japanese Patent Office on Jun. 10, 2014 for related Japanese Patent Application No. JP2013-546566.
Harvey et al., Stud. Surf. Sci. Catal., 49, 411-420 (1989).
Rouse, R. C. et al., N. Jb. Miner. Mh., 10, 433-440 (1987).
Robson, H. E. et al., Adv. Chem. Ser., 121, 106-115.
G.M. Johnson et al., AlGeO Microporous Mesoporous Mat., 28, 139-154 (1999).
Gler et al., Nature, 349, 508-510 (1991).
Newsam et al., J. Phys. Chem., 99, 9924-9932 (1995).
Feng, P. Y. et al., Microporous Mesoporous Mat., 23, 315-322 (1998).
Tan et al., Microporous and Mesoporous Materials 53, 97-108 (2002).
G. Liu et al., Microporous and Mesoporous Materials 114, 416-423 (2008).
Patent Examination Report issued by Australian Patent Office on Apr. 21, 2014 for related Australian Patent Application No. 2011349908.
The first Office Action issued by Korean Patent Office on Aug. 26, 2014 for related Korean patent application No. 10-2013-7019783.
The Search report and written opinion issued by Singapore Patent Office on Jul. 3, 2014 for related Singapore patent application No. 2013050968.
Rosseinsky, M.J. Microporous and Mesoporous Materials, vol. 73, pp. 15-30, 2004.

* cited by examiner

SOLVOTHERMAL SYNTHESIS PROCESS OF SAPO MOLECULAR SIEVES AND CATALYSTS PREPARED THEREBY

PRIORITY CLAIM

This is a U.S. national stage of application No. PCT/CN2011/076332, filed on Jun. 24, 2011. Priority is claimed on the following application: Country: China, Application No.: 201010610515.5, Filed: Dec. 29, 2010, the content of which is incorporated here by reference.

TECHNICAL FIELD

The present invention relates to a process for synthesizing SAPO molecular sieves.

The present invention also relates to the catalyst application of the above described material in conversion reactions of oxygen-containing compounds to low carbon olefins.

BACKGROUND ART

Since a series of aluminum phosphate molecular sieves and derivatives thereof were successively synthesized in 1982 by Union Carbide Corporation, US, in U.S. Pat. No. 4,310,440, aluminum phosphate molecular sieves and the heteroatom substituted derivatives are continuously one of research hotspots in the material field and catalyst field. This kind of SAPO molecular sieve synthesis technologies are characterized in that a silicon source, an aluminum source, a phosphorus source, and various template agents are employed in the synthesis, and the structural unit is composed of $PO^{2+}$, $AlO^{2-}$, and $SiO_2$ tetrahedrons. Among this kind of molecular sieves, some molecular sieves having a microporous structure such as SAPO-34 have been successfully applied to the MTG, MTO processes and so on, and show excellent catalyzing performance.

The synthesis of SAPO molecular sieve generally employs a hydrothermal process, in which water is used as the continuous phase and the main solvent, and the molar ratio of water to organic amine template agent is generally larger than 10. The synthesis results in a large amount of waste liquids which are difficult to be utilized, increasing the loadings of environmental treatment. Meanwhile, the synthesis process has a relative low yield which is generally less than 80%. This is mainly due to the fact that the precursor formed by the synthesis raw materials has a relatively high solubility in the aqueous solution.

Taking SAPO-34 as an example, SAPO-34 is a chabasite-type (CHA) molecular sieve, having ellipsoidal cages of eight-membered rings formed by packing double six-membered rings in ABC manner and a three dimension crossing channel structure, wherein the pore size is 0.38×0.38 nm, and the cage size is 1.0×0.67 nm, belonging to microporous molecular sieve. The space symmetry group thereof is R3m, belonging to trigonal system. SAPO-34 is composed of four elements of Si, Al, P, and O, with a composition alterable in a certain range, generally $n(Si)<n(P)<n(Al)$. The framework thereof is composed of $SiO_4$, $AlO_4^-$, and $PO_4^+$ tetrahedrons, wherein three kinds of bonds of [Al—O—P], [Si—O—Al] and [Si—O—Si] are present, but no [Si—O—P] bonds exist.

Traditionally, SAPO-34 molecular sieve is generally produced by a hydrothermal synthesis process which uses water as the solvent and is conducted in a sealed autoclave. The components for the synthesis comprise an aluminum source, a silicon source, a phosphorus source, a template agent, and deionized water. The silicon source may be chosen from silica sol, active silica, and orthosilicate ester. The aluminum source may be active alumina, pseudo boehmite, or alkoxy aluminum. Preferable silicon source and aluminum source are silica sol and pseudo boehmite. Phosphorus source is generally 85% phosphoric acid. The template agent commonly used comprises tetraethyl ammonium hydroxide (TEAOH), morpholine (MOR), piperidine, isopropylamine (i-PrNH2), triethylamine (TEA), diethylamine (DEA), dipropylamine, and the like, and a mixture thereof.

In the traditional hydrothermal synthesis of SAPO-34, the molar amount of the organic amine template agent used is significantly less than the molar amount of water, and as the amount of the template agent gradually increases, both of the product yield and crystallinity decrease to some degrees, see Table 1 in Microporous and Mesoporous Materials, 2008, 114(1-3): 4163.

As another type of SAPO molecular sieve, RHO-SAPO molecular sieve having a RHO framework structure is formed by connecting α cages through double eight-membered rings, belonging to cubic crystal system, and the main channel is composed of double eight-membered rings, having an opening size of 0.36 nm×0.36 nm. In 1973, Robson, H. E. et al. firstly reported that a silicon-aluminum zeolite molecular sieve with a RHO structure was synthesized using $Na^+$ and $Cs^+$ as structure directing agents (Adv. Chem. Ser., 121, 106-115). In 1987, Rouse, R. C. et al. reported the discovery of one kind of natural ores having RHO structure (N. Jb. Miner. Mh., 1987, 433-440). Henceforth, BePO (Stud. Surf. Sci. Catal., 1989, 49, 411-420), AlGeO (Microporous Mesoporous Mat., 1999, 28, 139-154), BeAsO (1991, Nature, 349, 508-510), and GaSiO (J. Phys. Chem., 1995, 99, 9924-9932) molecular sieves having RHO structure were successively synthesized using $Na^+$ and $Cs^+$ as the structure directing agents. In 1998, Feng, P. Y. et al. reported that CoAPO—RHO, MgAPO—RHO, and MnAPO—RHO molecular sieves were synthesized using N,N'-diisopropyl-1,3-propanediamine as template agent (Microporous Mesoporous Mat., 23, 315-322).

The synthesis processes of RHO-SAPO molecular sieve mainly include a hydrothermal synthesis of RHO-SAPO with the participation of surfactant and a dry gel synthesis process without the participation of surfactant (see Chinese patent application No. 200910169329.X). For the hydrothermal synthesis process with the participation of surfactant, in one aspect, because the synthesis process employs water as the continuous phase and as the main solvent of the synthesis system, a large amount of waste liquid difficult to be utilized will be produced after the synthesis, increasing the loadings of environmental treatment; on the other hand, the synthesis process employs the relatively expensive surfactant, increasing the synthesis cost. In the dry gel synthesis process without the participation of surfactant, it requires to formulate a silicon-phosphorus-aluminum dry gel firstly, which involves a complicated process; the crystallinity of the RHO-SAPO molecular sieve obtained by this synthesis process is not high, and the obtained RHO-SAPO molecular sieve is generally difficult to be separated through the manner of washing and so on from the uncrystallized silicon-phosphorus-aluminum dry gel.

For solving the problems in the above described SAPO synthesis processes, the present inventors attempt to synthesize SAPO by a solvothermal synthesis process, that is, to synthesize SAPO molecular sieves by employing a non-water medium as the main solvent, and it is surprisingly found that, various kinds of SAPO molecular sieves can be successfully synthesized in the case where an organic amine is used as both the main solvent and the template agent of the synthesis system, in the presence of only a small amount of water.

DISCLOSURE OF THE INVENTION

An object of the present invention is to provide a process for synthesizing SAPO molecular sieves in solvothermal systems.

In order to achieve the above described object, the present invention employs organic amines as the organic solvent and the template agents of the solvothermal synthesis systems, to synthesize SAPO molecular sieves in the presence of small amount of water.

Specifically, the present invention provides a solvothermal synthesis process of SAPO molecular sieves, comprising the following synthesis steps:

a) an organic amine, an aluminum source, a phosphorus source, a silicon source, and water are mixed in a molar ratio of 6-30:1:0.5-5:0.01-1.0:0.1-15, to obtain an initial mixture for preparing the SAPO molecular sieves, wherein the molar ratio of water to the organic amine is less than 2.0;

b) the initial mixture obtained in the step a) is maintained at 30-60° C., and aged with mixing for not more than 24 hours, to obtain an initial gel;

c) the initial gel obtained in the step b) is crystallized at 150-250° C. for 0.5-15 days.

In the synthesis process of the present invention, the initial mixture in the preparation of SAPO molecular sieves may further comprises an organic alcohol, and the molar ratio of the organic amine, the aluminum source, the phosphorus source, the silicon source, the organic alcohol and water in the initial mixture is 6-30:1:0.5-5:0.01-1.0:0.01-0.50:0.1-15.

In the synthesis process of the present invention, the molar ratio of the organic amine/water is larger than 0.51, preferably larger than 1.0, more preferably lager than 1.5, most preferably lager than 3.0, and less than 300; the aging time is 0-24 h, preferably 0.5-15 h; and the crystallization time is 0.5-15 days, preferably 1-7 days.

The process of the present invention further comprises a step of separating, washing, and drying the crystallized product of step c), to obtain as-synthesized SAPO-molecular sieves.

The aluminum source used in the present invention is any one of pseudo boehmite, aluminium isopropoxide, alumina, aluminum hydroxide, aluminum chloride, and aluminum sulfate or a mixture thereof; the phosphorus source used is any one of orthophosphoric acid, metaphosphoric acid, a phosphate, and a phosphite or a mixture thereof; the silicon source used is any one of silica sol, ethyl orthosilicate, white carbon black, and silica or a mixture thereof; the organic amine used is any one of an organic primary, secondary, and tertiary amine or a mixture thereof, comprising any one of morpholine, piperidine, isopropylamine, triethylamine, diethylamine, di-n-propylamine, diisopropylamine, hexamethyleneimine, N',N',N,N-tetramethyl-1,6-hexanediamine, and N,N-diisopropylethylamine or a mixture thereof, and preferably any one of diethylamine, triethylamine, morpholine, hexamethyleneimine, and N,N-diisopropylethylamine or a mixture thereof.

The organic alcohol used in the initial mixture is any one of methanol, ethanol, n-propanol, and i-propanol or a mixture thereof. In the synthesis of SAPO molecular sieves, especially in the synthesis of SAPO-34, SAPO-18, SAPO-35, or SAPO-56 molecular sieve, the addition of the organic alcohol is mainly for the purpose of suppressing the formation of impure crystal phase, thereby ensuring the re-productivity of the synthesis process and high purity.

In the present invention, the prepared SAPO molecular sieve is any one of SAPO-5, SAPO-34, SAPO-11, SAPO-17, SAPO-18, SAPO-31, SAPO-35, SAPO-40, SAPO-41, SAPO-43, SAPO-56, and RHO-SAPO or a mixture thereof.

In the present invention, the initially prepared synthesis mixture is aged with mixing at 30-60° C. for a period of time, and the main effect of this process is to efficiently increase the crystallinity of the product, while improving the yield.

The synthesized SAPO molecular sieves, after being calcined at 400-700° C. in the air, may be used as catalysts for acid-catalyzed reactions.

The synthesized SAPO molecular sieves, after being calcined at 400-700° C. in the air, may also be used as catalysts for conversion reactions of oxygen-containing compounds to olefins.

The present invention can bring about the advantages as follows:

(1) The synthesis yield is high, which is generally more than 90% (calculation method: dry basis mass of the product/total dry basis mass of the fed oxides×100%);

(2) Because the amount of water used is relatively small in the synthesis and the respective inorganic raw materials and synthesis precursors are difficult to be dissolved in the organic amine, the organic amine may be easily separated from the gel product, recovered and reused after the synthesis, and the amount of waste liquid produced is low.

(3) The prepared SAPO shows excellent catalyzing performance in the methanol-to-olefin conversion reaction. For example, with the prepared SAPO-34 herein, as compared with the SAPO-34 molecular sieve prepared by a general hydrothermal synthesis process, the reaction lifetime is longer, and the selectivity for ethylene and propylene is improved to a certain degree.

SPECIFIC EMBODIMENTS OF THE INVENTION

Figure 1:
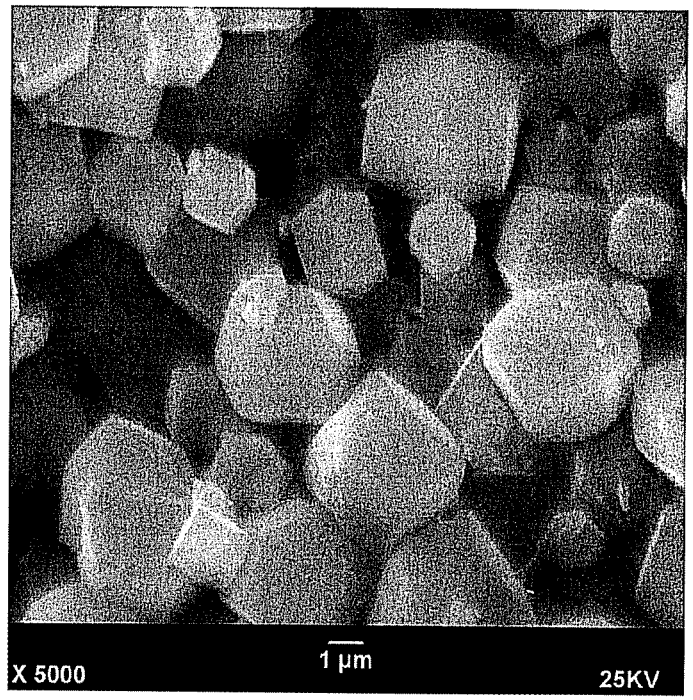
FIG. 1 is a scanning electron microscope (SEM) image of the synthesized product in Example 10 of the present invention.

The present invention will be described in details by Examples, but the present invention is not limited to these Examples.

Example 1

7.03 g of active alumina ($Al_2O_3$ mass percent of 72.5%) were mixed homogeneously with 60 ml of triethylamine by stirring, into which 10.30 g of orthophosphoric acid ($H_3PO_4$ mass percent of 85%), 5.69 g of silica sol ($SiO_2$ mass percent of 28.2%), 0.50 g of ethanol, and 0.3 g of deionized water were sequentially added under stirring, then the mixture was vigorously stirred to be mixed homogeneously. After stirring at 40° C. for 10 h, the gel was transferred into a stainless steel reaction kettle, and dynamically synthesized at a crystallization temperature of 180° C. for 60 hours. After the crystallization, the solid product was centrifuged, washed, and dried at 100° C. in the air, obtaining 14.1 g of as-synthesized product (calcination weight loss of 15%). The sample was subjected to XRD analysis. XRD data were shown in Table 1, and the results indicated that the synthesized product was SAPO-34 molecular sieve.

Comparative Example 1

The formulation ratio and the crystallization process were the same as Example 1, but the addition of ethanol was omitted. After the crystallized product was washed and dried, XRD analysis was conducted, and the results indicated that the sample was SAPO-34 containing a small amount of SAPO-5, where a peak height ratio of the first strongest peaks of the two products was: SAPO-5/SAPO-34=1/9.

Comparative Example 2

SAPO-34 was synthesized by a conventional hydrothermal synthesis process, see Microporous and Mesoporous Materials 53 (2002) 97-108.

7.03 g of active alumina ($Al_2O_3$ mass percent of 72.5%), 10.3 g of orthophosphoric acid ($H_3PO_4$ mass percent of 85%), 5.69 g of silica sol ($SiO_2$ mass percent of 28.2%), and 35 ml of deionized water were mixed homogeneously by stirring, and into which 21 ml of triethylamine were added under stirring. After the mixture was vigorously stirred to be mixed homogeneously, the gel was transferred into a stainless steel reaction kettle, and dynamically synthesized at a crystallization temperature of 200° C. for 48 hours. After the crystallization was finished, the solid product was centrifuged, washed, and dried at 100° C. in the air, obtaining 11.0 g of as-synthesized product (calcination weight loss of 15.5%). The sample was subjected to XRD analysis, and the results indicated that the synthesized product was SAPO-34 molecular sieve.

Example 2

7.03 g of active alumina ($Al_2O_3$ mass percent of 72.5%) were mixed homogeneously with 50 ml of diethylamine and 15 ml of triethylamine by stirring, into which 9.5 g of orthophosphoric acid ($H_3PO_4$ mass percent of 85%), 4.55 g of silica sol ($SiO_2$ mass percent of 28.2%), and 0.38 g of methanol were added at one time under stirring, and then vigorously stirred to be mixed homogeneously. After the mixture was stirred at 55° C. for 12 h, the gel was transferred into a stainless steel reaction kettle, and dynamically synthesized at a crystallization temperature of 180° C. for 100 hours. After the crystallization was finished, the solid product was centrifuged, washed, and dried at 100° C. in the air, obtaining 13.0 g of as-synthesized product (calcination weight loss of 14.1%). The sample was subjected to XRD analysis. The XRD data were shown in Table 2. The results indicated that the synthesized product was SAPO-34 molecular sieve.

Comparative Example 3

The formulation ratio and the crystallization process were the same as Example 2, but the addition of methanol was omitted. After the crystallized product was washed and dried, it was subjected to XRD analysis. The results indicated that the sample was SAPO-34 containing a small amount of SAPO-5. The peak height ratio of the first strongest peaks of the two products was: SAPO-5/SAPO-34=1/11.

Example 3

7.03 g of active alumina ($Al_2O_3$ mass percent of 72.5%) were mixed homogeneously with 23.13 ml of triethylamine and 60 ml of morpholine by stirring, into which 10.30 g of orthophosphoric acid ($H_3PO_4$ mass percent of 85%), 4.55 g of silica sol ($SiO_2$ mass percent of 28.2%), 1.0 g of ethanol, and 2.04 g of deionized water were added at one time under stirring, and then vigorously stirred to be mixed homogeneously. After stirring at 35° C. for 12 h, the gel was transferred into a stainless steel reaction kettle, and dynamically synthesized at a crystallization temperature of 210° C. for 24 hours. The solid product was centrifuged, washed with deionized water to neutral pH, and after drying at 100° C. in the air, 13.6 g of as-synthesized product (calcination weight loss of 14.5%) were obtained. The sample was subjected to XRD analysis, and the data were shown in Table 3. XRD data showed that the synthesized product was SAPO-34 molecular sieve.

Comparative Example 4

The formulation ratio and the crystallization process were the same as Example 3, but the low temperature aging process was omitted. After the crystallized product was washed and dried, 11.5 g of as-synthesized product (calcination weight loss of 16.1%) were obtained. It was subjected to XRD analysis. The results indicated that the sample was pure SAPO-34, having a relative crystallinity of 80% (the relative crystallinity of FDZ-38-3 was defined as 100%).

Example 4

Same as Example 3, except that 1.0 g of ethanol were changed to 1.0 g of n-propanol, the other components and crystallization conditions were unchanged. The crystallized product was subjected to XRD diffraction analysis. The results indicated that the synthesized sample was SAPO-34 molecular sieve.

Example 5

Same as Example 3, except that 7.03 g of active alumina were changed to 20.65 g of aluminium isopropoxide and the amount of deionized water was changed to 1.0 g, the other components and crystallization conditions were unchanged. The crystallized product was subjected to XRD diffraction analysis. The results indicated that the synthesized sample was SAPO-34 molecular sieve.

Example 6

Same as Example 1, except that 7.03 g of active alumina were, changed to 20.65 g of aluminium isopropoxide, 5.69 g of silica sol ($SiO_2$ mass percent of 28.2%) were changed to 1.6 g of fumed silica, and the amount of deionized water was changed to 1.0 g, the other components and crystallization conditions were unchanged. The crystallized product was subjected to XRD diffraction analysis. The results indicated that the synthesized sample was SAPO-34 molecular sieve.

Example 7

Same as Example 1, except that 7.03 g of active alumina were changed to 5.2 g of γ-alumina, 5.69 g of silica sol ($SiO_2$ mass percent of 28.2%) were changed to 1.6 g of fumed silica, and the amount of deionized water was changed to 0.1 g, the other components and crystallization conditions were unchanged. The crystallized product was subjected to XRD diffraction analysis. The results indicated that the synthesized sample was SAPO-34 molecular sieve.

Example 8

Same as Example 1, except that 7.03 g of active alumina calcined at a high temperature of 600° C. (the water content therein was removed) were used as the aluminum source, 5.69 g of silica sol ($SiO_2$ mass percent of 28.2%) were changed to 1.6 g of fumed silica, and the amount of deionized water was changed to 0.1 g, the other components and crystallization conditions were unchanged. The crystallized product was subjected to XRD diffraction analysis, and the results indicated that the synthesized sample was SAPO-34 molecular sieve.

Example 9

The samples obtained in Example 1, Comparative Example 2, and Example 7 were aerated with air and calcined at 600° C. for 4 hours. Then they were pressed into tablets, and crashed to 20-40 mesh. 1.0 g of sample was weighted, loaded into a fixed bed reactor, and subjected to MTO reaction evaluation. Nitrogen gas was introduced and the sample was activated at 550° C. for 1 hour, after that, the temperature was decreased to 450° C. to conduct the reaction. Methanol was carried by nitrogen gas at a flow rate of 40 ml/min, and the weight space velocity of methanol was $2.0\ h^{-1}$. The reaction product was analyzed by on-line gas chromatography. The results were shown in Table 4.

TABLE 1

XRD results of the sample in Example 1

| No. | 2θ | d(Å) | 100 × I/I$_0$ |
|---|---|---|---|
| 1 | 9.4838 | 9.32578 | 100 |
| 2 | 12.8384 | 6.89556 | 13.12 |
| 3 | 13.9703 | 6.33933 | 2.59 |
| 4 | 16.0023 | 5.53863 | 36.38 |
| 5 | 16.9215 | 5.23976 | 2.91 |
| 6 | 19.0086 | 4.66891 | 0.95 |
| 7 | 20.5561 | 4.32079 | 41.4 |
| 8 | 21.2911 | 4.17326 | 2.84 |
| 9 | 23.0914 | 3.8518 | 2.39 |
| 10 | 24.099 | 3.69299 | 0.76 |
| 11 | 25.0766 | 3.5512 | 1.05 |
| 12 | 25.8444 | 3.44741 | 7.99 |
| 13 | 27.5828 | 3.23396 | 1.17 |
| 14 | 28.1603 | 3.16895 | 0.81 |
| 15 | 29.5158 | 3.02642 | 1.81 |
| 16 | 30.5066 | 2.93035 | 2.61 |
| 17 | 31.048 | 2.88048 | 5.06 |
| 18 | 36.1308 | 2.48607 | 0.77 |
| 19 | 43.238 | 2.09248 | 0.71 |
| 20 | 49.0196 | 1.85836 | 3.63 |
| 21 | 50.9873 | 1.79117 | 0.45 |
| 22 | 53.1682 | 1.7213 | 1.17 |

TABLE 2

XRD results of the sample in Example 2

| No. | 2θ | d(Å) | 100 × I/I$_0$ |
|---|---|---|---|
| 1 | 9.4545 | 9.35457 | 100 |
| 2 | 12.8344 | 6.8977 | 20.88 |
| 3 | 13.9189 | 6.3626 | 3.38 |
| 4 | 15.9622 | 5.55246 | 40.27 |
| 5 | 17.6853 | 5.01515 | 25.06 |
| 6 | 18.5142 | 4.79245 | 3.12 |
| 7 | 18.9682 | 4.67876 | 4.28 |
| 8 | 20.5336 | 4.32546 | 93.44 |
| 9 | 21.9097 | 4.05682 | 14.49 |
| 10 | 22.3181 | 3.98348 | 5.92 |
| 11 | 22.9725 | 3.87147 | 15.98 |
| 12 | 24.8162 | 3.58786 | 54.74 |
| 13 | 25.8284 | 3.44951 | 20.2 |
| 14 | 26.2107 | 3.40006 | 1.71 |
| 15 | 27.5669 | 3.23579 | 8.67 |
| 16 | 28.0275 | 3.18365 | 6.6 |
| 17 | 29.4615 | 3.03188 | 3.28 |
| 18 | 30.5062 | 2.92796 | 38.81 |
| 19 | 30.6299 | 2.92367 | 23.27 |
| 20 | 30.9433 | 2.88759 | 24.57 |
| 21 | 31.4801 | 2.83956 | 3.43 |
| 22 | 32.2688 | 2.77194 | 1.71 |
| 23 | 33.3591 | 2.68379 | 3.55 |
| 24 | 34.4001 | 2.60492 | 7.23 |
| 25 | 34.8399 | 2.57304 | 1.75 |
| 26 | 35.8666 | 2.50171 | 5.66 |
| 27 | 38.3234 | 2.34679 | 1.02 |
| 28 | 39.5752 | 2.27539 | 3.71 |
| 29 | 42.6257 | 2.11935 | 3.96 |
| 30 | 43.2903 | 2.08834 | 4 |
| 31 | 47.5413 | 1.91105 | 4.05 |
| 32 | 48.6651 | 1.86951 | 5.82 |
| 33 | 49.0438 | 1.85596 | 3.29 |

TABLE 3

XRD result of the sample in Example 3

| No. | 2θ | d(Å) | 100 × I/I$_0$ |
|---|---|---|---|
| 1 | 9.4514 | 9.35767 | 100 |
| 2 | 12.8291 | 6.90055 | 21.49 |
| 3 | 13.9125 | 6.3655 | 3.09 |
| 4 | 14.3377 | 6.17767 | 0.89 |
| 5 | 15.9594 | 5.5534 | 40.06 |
| 6 | 17.6902 | 5.01377 | 25.47 |
| 7 | 18.5204 | 4.79087 | 2.74 |
| 8 | 18.9616 | 4.68036 | 4.21 |
| 9 | 20.5265 | 4.32694 | 99.51 |
| 10 | 21.9084 | 4.05705 | 14.3 |
| 11 | 22.3198 | 3.98319 | 5.43 |
| 12 | 22.9648 | 3.87275 | 15.44 |
| 13 | 24.8165 | 3.58782 | 55.86 |
| 14 | 25.8241 | 3.45008 | 19.99 |
| 15 | 27.5629 | 3.23626 | 7.53 |
| 16 | 28.038 | 3.18249 | 5.87 |
| 17 | 29.4517 | 3.03286 | 4.03 |
| 18 | 30.4977 | 2.92876 | 39.05 |
| 19 | 30.633 | 2.92338 | 21.65 |
| 20 | 30.9388 | 2.888 | 25.98 |
| 21 | 31.4775 | 2.8398 | 3.24 |
| 22 | 32.2567 | 2.77296 | 1.81 |
| 23 | 33.3489 | 2.68459 | 3.5 |
| 24 | 34.3856 | 2.60599 | 7.75 |
| 25 | 34.8176 | 2.57463 | 2.19 |
| 26 | 35.8657 | 2.50177 | 6.32 |
| 27 | 38.1446 | 2.35738 | 0.91 |
| 28 | 39.1675 | 2.29814 | 0.95 |
| 29 | 39.5678 | 2.2758 | 3.48 |
| 30 | 42.6337 | 2.11897 | 4.78 |
| 31 | 43.2908 | 2.08832 | 3.63 |
| 32 | 44.9355 | 2.01563 | 0.64 |
| 33 | 47.5282 | 1.91155 | 3.84 |
| 34 | 48.6704 | 1.86932 | 5.17 |
| 35 | 49.0618 | 1.85532 | 2.93 |

TABLE 4

Results of the samples for methanol-to-olefin conversion reaction

| Sample | Lifetime (min) | Selectivity (mass %)* | | | | | | | |
|---|---|---|---|---|---|---|---|---|---|
| | | $CH_4$ | $C_2H_4$ | $C_2H_6$ | $C_3H_6$ | $C_3H_8$ | $C_4^+$ | $C_5^+$ | $C_2H_4 + C_3H_6$ |
| Example 1 | 160 | 2.2 | 45.9 | 0.8 | 39.5 | 1.2 | 8.5 | 1.9 | 85.4 |
| Comparative Example 2 | 140 | 2.7 | 44.3 | 0.8 | 38.1 | 1.9 | 10.1 | 2.1 | 82.4 |
| Example 7 | 160 | 2.3 | 44.8 | 0.7 | 39.9 | 1.6 | 9.0 | 1.7 | 84.7 |

*The highest (ethylene + propylene) selectivity in the case of 100% methanol conversion Example 10

10.37 g of orthophosphoric acid ($H_3PO_4$ mass percent of 85%) were added into 60 ml of diethylamine under the condition of ice water bath. 8.34 g of active alumina ($Al_2O_3$ mass percent of 72.5%), 5.69 g of silica sol ($SiO_2$ mass percent of 28.2%), and 0.2 g of deionized water were sequentially added thereto under stirring condition, and vigorously stirred so as to be mixed homogeneously. The gel was transferred into a stainless steel reaction kettle, and dynamically synthesized at a crystallization temperature of 200° C. for 48 hours. After the crystallization was finished, the solid product was centrifuged, washed, and dried at 100° C. in the air, and the sample was then subjected to XRD analysis. The XRD data were shown in Table 5. The results indicated that the synthesized product had a RHO structure. The composition of the sample was $Al_{0.489}P_{0.306}Si_{0.205}$ according to XRF analysis, indicating that the obtained sample was RHO-SAPO molecular sieve. The obtained sample was characterized by scanning electron microscope, and the resultant electron microscope photograph was shown in FIG. 1.

Comparative Example 5

8.34 g of active alumina ($Al_2O_3$ mass percent of 72.5%) were homogeneously mixed with 60 ml of diethylamine, and into which 10.37 g of orthophosphoric acid ($H_3PO_4$ mass percent of 85%), 5.69 g of silica sol ($SiO_2$ mass percent of 28.2%), and 0.2 g deionized water were sequentially added under stirring. After vigorously stirring to make the mixture mixed homogeneously, the gel was transferred into a stainless steel reaction kettle, and dynamically synthesized at a crystallization temperature of 200° C. for 48 hours. After the crystallization was finished, the solid product was centrifuged, washed, and dried at 100° C. in the air, and the sample was then subjected to XRD analysis. XRD results indicated that the synthesized product was the mixed crystal of RHO-SAPO and SAPO-34 molecular sieves.

Comparative Example 6

8.34 g of active alumina ($Al_2O_3$ mass percent of 72.5%), 10.37 g orthophosphoric acid ($H_3PO_4$ mass percent of 85%), 5.69 g of silica sol ($SiO_2$ mass percent of 28.2%), and 45 ml of deionized water were homogeneously mixed, into which 10 ml of diethylamine were added under stirring. After vigorously stirring to make the mixture mixed homogeneously, the gel was transferred into a stainless steel reaction kettle, and dynamically synthesized at a crystallization temperature of 200° C. for 48 hours. After the crystallization was finished, the solid product was centrifuged, washed, and dried at 100° C. in the air. The sample was subjected to XRD analysis, and the results indicated that synthesized product was SAPO-34 molecular sieve.

Example 11

Same as Example 10, except that 8.34 g of active alumina were changed to 24.5 g of aluminium isopropoxide, and the amount of deionized water was changed to 1.0 g, the other components and crystallization conditions were unchanged. The crystallized product was subjected to XRD diffraction analysis. The results indicated that the synthesized sample was RHO-SAPO molecular sieve.

Comparative Example 7

Same as Example 10, except that 8.34 g of active alumina were changed to 24.5 g of aluminium isopropoxide, and the amount of deionized water was changed to 10 g, the other components and crystallization conditions were unchanged. The crystallized product was subjected to XRD diffraction analysis. The results indicated that the synthesized sample was SAPO-34 molecular sieve.

Example 12

Figure 2:
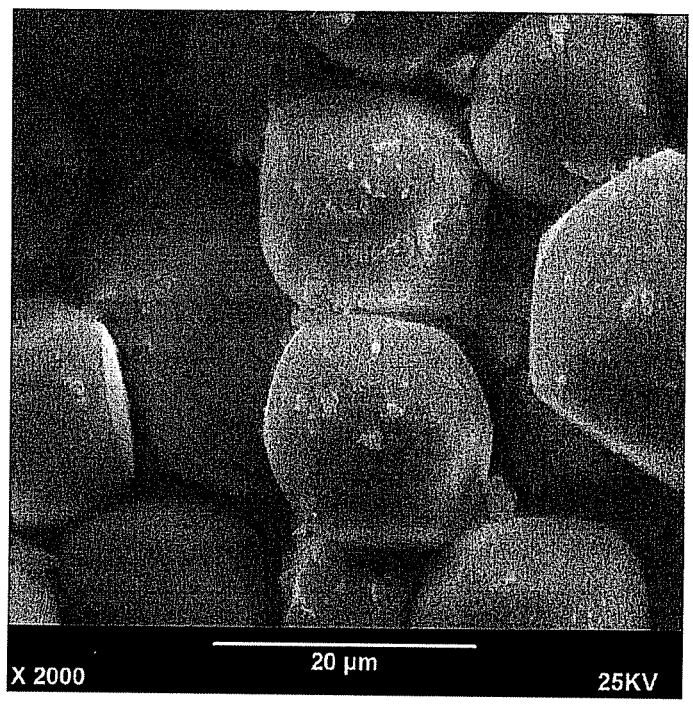
FIG. 2 is the scanning electron microscope (SEM) image of synthesized product in Example 12 of the present invention.

11.52 g of orthophosphoric acid ($H_3PO_4$ mass percent of 85%) were added into a mixed solution of 60 ml of diethylamine and 15 ml of triethylamine under the condition of ice water bath, and into which 7.03 g of active alumina ($Al_2O_3$ mass percent of 72.5%), 4.55 g of silica sol ($SiO_2$ mass percent of 28.2%), and 0.1 g of deionized water were sequentially added under stirring. After vigorously stirring to make the mixture mixed homogeneously, the gel was transferred into a stainless steel reaction kettle, and was dynamically synthesized at a crystallization temperature of 190° C. for 48 hours. After the crystallization was finished, the solid product was centrifuged, washed, and dried at 100° C. in the air, and the sample was then subjected to XRD analysis. XRD data were shown in Table 6. The results indicated that synthesized product had a RHO structure. The obtained sample was characterized by scanning electron microscope, and the resultant electron microscope photograph was shown in FIG. 2.

Example 13

Same as Example 10, except that 8.34 g of active alumina were changed to 24.5 g of aluminium isopropoxide, 5.69 g of silica sol ($SiO_2$ mass percent of 28.2%) were changed to 1.6 g of fumed silica, and the amount of deionized water was changed to 1.2 g, the other components and crystallization conditions were unchanged. The crystallized product was subjected to XRD diffraction analysis. The results indicated that the synthesized sample was RHO-SAPO molecular sieve.

Example 14

Same as Example 10, except that 8.34 g of active alumina were changed to 6.1 g of γ-alumina, and 5.69 g of silica sol ($SiO_2$ mass percent of 28.2%) were changed to 1.6 g of fumed silica, the other components and crystallization conditions were unchanged. The crystallized product was subjected to XRD diffraction analysis. The results indicated that the synthesized sample was RHO-SAPO molecular sieve.

Example 15

Same as Example 10, except that 60 ml of diethylamine were changed to a mixed solution of 60 ml of diethylamine and 18 ml of morpholine, the amount of phosphoric acid (85 wt %) was changed to 12.35 g, and the amount of deionized water was changed to 0.5 g, the other components and crystallization conditions were unchanged. The obtained product was marked as FDZ-31-2. XRD diffraction analysis results were shown in Table 7. The results indicated that the synthesized product was RHO-SAPO molecular sieve.

TABLE 5

XRD results of the sample in Example 10

| No. | $2\theta$ | d(Å) | $100 \times I/I_0$ |
|---|---|---|---|
| 1 | 8.2149 | 10.76318 | 100 |
| 2 | 11.6288 | 7.60998 | 6.49 |
| 3 | 14.2579 | 6.21209 | 54.61 |
| 4 | 16.4743 | 5.381 | 22.21 |
| 5 | 18.4368 | 4.81239 | 21.81 |
| 6 | 20.2103 | 4.39393 | 6.4 |
| 7 | 21.8497 | 4.06781 | 35.21 |
| 8 | 23.3771 | 3.80537 | 9.48 |
| 9 | 24.8198 | 3.58735 | 46.77 |
| 10 | 26.1863 | 3.40317 | 62.07 |
| 11 | 28.7405 | 3.10628 | 17.34 |
| 12 | 29.94 | 2.9845 | 29.97 |
| 13 | 32.2224 | 2.77812 | 23.32 |
| 14 | 35.3993 | 2.53575 | 15.54 |
| 15 | 41.9817 | 2.15214 | 2.79 |
| 16 | 43.7264 | 2.06852 | 6.33 |
| 17 | 47.0375 | 1.93194 | 7.7 |
| 18 | 47.8344 | 1.90159 | 7.46 |
| 19 | 48.6516 | 1.87155 | 3.14 |
| 20 | 49.424 | 1.84409 | 1.44 |
| 21 | 50.9384 | 1.79277 | 7.34 |
| 22 | 54.7545 | 1.67067 | 4.44 |
| 23 | 56.8143 | 1.62052 | 1.23 |
| 24 | 57.4795 | 1.60201 | 5.14 |

TABLE 6

XRD results of the sample in Example 12

| No. | $2\theta$ | d(Å) | $100 \times I/I_0$ |
|---|---|---|---|
| 1 | 8.2168 | 10.76076 | 100 |
| 2 | 11.6307 | 7.60871 | 5.72 |
| 3 | 14.2605 | 6.21094 | 54.77 |
| 4 | 16.48 | 5.37915 | 18.84 |
| 5 | 18.437 | 4.81235 | 19.03 |
| 6 | 20.2168 | 4.39252 | 5.09 |
| 7 | 21.8576 | 4.06636 | 32.43 |
| 8 | 23.3892 | 3.80343 | 8.85 |
| 9 | 24.8322 | 3.58559 | 44.47 |
| 10 | 26.1985 | 3.40161 | 54.73 |
| 11 | 28.7666 | 3.10351 | 14.45 |
| 12 | 29.9569 | 2.98286 | 28.75 |
| 13 | 32.2382 | 2.7768 | 21.63 |
| 14 | 35.4144 | 2.5347 | 15.12 |
| 15 | 41.9265 | 2.10811 | 2.63 |
| 16 | 43.7355 | 2.06982 | 5.39 |
| 17 | 47.0589 | 1.92951 | 6.95 |
| 18 | 47.8646 | 1.89889 | 6.73 |
| 19 | 48.6834 | 1.8704 | 2.66 |
| 20 | 49.4289 | 1.84391 | 1.63 |
| 21 | 50.9569 | 1.79216 | 6.91 |
| 22 | 54.7386 | 1.67368 | 2.34 |
| 23 | 56.0994 | 1.63811 | 4.6 |
| 24 | 57.4955 | 1.60161 | 4.53 |

TABLE 7

XRD results of the sample in Example 15

| No. | $2\theta$ | d(Å) | $100 \times I/I_0$ |
|---|---|---|---|
| 1 | 8.2217 | 10.75434 | 100 |
| 2 | 11.637 | 7.60463 | 5.86 |
| 3 | 14.2673 | 6.20799 | 55.11 |
| 4 | 16.4873 | 5.37676 | 19.21 |
| 5 | 18.449 | 4.80923 | 19.66 |
| 6 | 20.2242 | 4.39094 | 4.98 |
| 7 | 21.8654 | 4.06493 | 29.95 |
| 8 | 23.3978 | 3.80206 | 9.34 |
| 9 | 24.8392 | 3.5846 | 42.88 |
| 10 | 26.2065 | 3.40059 | 56.1 |
| 11 | 28.7624 | 3.10396 | 14.92 |
| 12 | 29.9631 | 2.98226 | 28.28 |
| 13 | 32.2449 | 2.77624 | 20.67 |
| 14 | 35.4242 | 2.53402 | 13.81 |
| 15 | 42.0138 | 2.15057 | 2.4 |
| 16 | 43.7605 | 2.0687 | 5.52 |
| 17 | 47.0754 | 1.93047 | 6.4 |
| 18 | 47.8707 | 1.90024 | 6.25 |
| 19 | 48.6616 | 1.86964 | 3.63 |
| 20 | 49.4318 | 1.84382 | 1.81 |
| 21 | 50.9796 | 1.79142 | 6.18 |
| 22 | 54.7219 | 1.67743 | 1.28 |
| 23 | 56.1134 | 1.63773 | 4.05 |
| 24 | 57.5244 | 1.60087 | 4.37 |

Example 16

Same as Example 1, except that the crystallization temperature was changed to 210° C., the crystallization time was changed to 48 h, and the silicon source was changed to 1.6 g of fumed silica. After the crystallization was finished, the solid product was centrifuged, washed, and dried at 100° C. in the air, obtaining 12.2 g of as-synthesized product (calcination weight loss of 14.0%). The sample was subjected to XRD analysis. The results indicated that synthesized product was SAPO-18 molecular sieve.

Example 17

Same as Example 1, except that the organic amine was changed to 65 ml of N',N-diisopropylethylamine, and the silicon source was changed to 1.6 g of fumed silica. After the crystallization was finished, the solid product was centrifuged, washed, and dried at 100° C. in the air, obtaining 12.6 g of as-synthesized product (calcination weight loss of 15.2%). The sample was subjected to XRD analysis. The results indicated that synthesized product was SAPO-18 molecular sieve.

Example 18

Same as Example 1, except that the organic amine was changed to 65 ml of N',N',N,N-tetramethyl-1,6-hexanediamine. After the crystallization was finished, the solid product was centrifuged, washed, and dried at 100° C. in the air, obtaining 13.6 g of as-synthesized product (calcination weight loss of 16.8%). The sample was subjected to XRD analysis. Results indicated that the synthesized product was SAPO-56 molecular sieve.

Example 19

Same as Example 1, except that the organic amine was changed to 60 ml of hexamethyleneimine. After the crystallization was finished, the solid product was centrifuged, washed, and dried at 100° C. in the air, obtaining 12.1 g of as-synthesized product (calcination weight loss of 13.8%). The sample was subjected to XRD analysis. The results indicated that synthesized product was SAPO-35 molecular sieve.

Example 20

Same as Example 1, except that the organic amine was changed to 65 ml of hexamethyleneimine, the crystallization temperature was changed to 205° C., and the crystallization time was changed to 48 h, the other conditions were unchanged. After the crystallization was finished, the solid product was centrifuged, washed, and dried at 100° C. in the air, obtaining 13.3 g of as-synthesized product (calcination weight loss of 14%). The sample was subjected to XRD analysis. The results indicated that synthesized product was SAPO-34 molecular sieve.

Example 21

Same as Example 1, except that the organic amine was changed to 60 ml of di-n-propylamine, the other conditions were unchanged. After the crystallization was finished, the solid product was centrifuged, washed, and dried at 100° C. in the air, obtaining 12.8 g of as-synthesized product (calcination weight loss of 14.2%). The sample was subjected to XRD analysis. The results indicated that the synthesized product was SAPO-43 molecular sieve.

The invention claimed is:

1. A solvothermal synthesis process of SAPO molecular sieves, wherein the main steps are as following:
   a) an organic amine, an aluminum source, a phosphorus source, a silicon source, and water are mixed in a molar ratio of 6-30:1:0.5-5:0.01-1.0:0.1-15, to obtain an initial mixture for preparing the SAPO molecular sieves, wherein the molar ratio of water to the organic amine is less than 2.0;
   b) the initial mixture obtained in the step a) is maintained at 30-60° C. and aged with stirring for not more than 24 hours, to obtain an initial gel;
   c) the initial gel obtain in the step b) is crystallized at 150-250° C. for 0.5-15 days.

2. The solvothermal synthesis process of SAPO molecular sieves according to claim 1, wherein the initial mixture for preparing the SAPO molecular sieves further comprises an organic alcohol therein.

3. The solvothermal synthesis process of SAPO molecular sieves according to claim 2, wherein the organic alcohol is any one of methanol, ethanol, n-propanol, and i-propanol or a mixture thereof.

4. The solvothermal synthesis process of SAPO molecular sieves according to claim 2, wherein the molar ratio of the organic amine, the aluminum source, the phosphorus source, the silicon source, the organic alcohol and water in the initial mixture is 6-30:1:0.5-5:0.01-1.0:0.01-0.50:0.1-15.

5. The solvothermal synthesis process of SAPO molecular sieves according to claim 1, wherein the aluminum source is any one of aluminium isopropoxide, alumina, aluminum hydroxide, aluminum chloride, and aluminum sulfate or a mixture thereof.

6. The solvothermal synthesis process of SAPO-molecular sieves according to claim 1, wherein the phosphorus source is any one of orthophosphoric acid, metaphosphoric acid, a phosphate, and a phosphite or a mixture thereof.

7. The solvothermal synthesis process of SAPO molecular sieves according to claim 1, wherein the silicon source is any one of silica sol, ethyl orthosilicate, and silica or a mixture thereof.

8. The solvothermal synthesis process of SAPO-34 molecular sieves according to claim 1, wherein the organic amine is any one of an organic primary, secondary, and tertiary amine or a mixture thereof.

9. The solvothermal synthesis process of SAPO-34 molecular sieves according to claim 1, wherein the organic amine is any one of morpholine, piperidine, isopropylamine, triethylamine, diethylamine, di-n-propylamine, diisopropylamine, hexamethyleneimine, N',N',N,N-tetramethyl-1,6-hexanediamine, and N,N-diisopropylethylamine or a mixture thereof.

10. The solvothermal synthesis process of SAPO molecular sieves according to claim 1, wherein the organic amine is any one of diethylamine, triethylamine, morpholine, hexamethyleneimine, and N,N-diisopropylethylamine or a mixture thereof.

11. The solvothermal synthesis process of SAPO molecular sieves according to claim 1, wherein the SAPO molecular sieve is any one of SAPO-5, SAPO-34, SAPO-11, SAPO-17, SAPO-18, SAPO-35, SAPO-40, SAPO-41, SAPO-43, SAPO-56, and RHO-SAPO or a mixture thereof.

12. The solvothermal synthesis process of SAPO molecular sieves according to claim 1, wherein the molar ratio of the organic amine to water is 0.51-300.

13. The solvothermal synthesis process of SAPO molecular sieves according to claim 1, wherein the molar ratio of the organic amine to water is 1.5-300.

14. The solvothermal synthesis process of SAPO molecular sieves according to claim 1, wherein the molar ratio of the organic amine to water is 3.0-300.

15. The solvothermal synthesis process of SAPO molecular sieves according to claim 1, wherein the aging time in the step b) is 0.5-15 h.

16. The solvothermal synthesis process of SAPO molecular sieves according to claim 1, wherein the crystallization time in the step c) is 1 to 7 days.

17. The solvothermal synthesis process of SAPO molecular sieves according to claim 1, wherein the process further comprises a step of separating, washing, and drying the crystallized product of step c).

18. Catalysts for acid-catalyzed reactions, which are synthesized by the solvothermal synthesis process of SAPO molecular sieves according to claim 1, and are calcined at 400-700° C. in air.

19. Catalysts for conversion reactions of oxygen-containing compounds to olefins, which are synthesized by the solvothermal synthesis process of SAPO molecular sieves according to claim 1, and are calcined at 400-700° C. in air.

* * * * *